United States Patent
Krihak et al.

[11] Patent Number: 5,810,989
[45] Date of Patent: Sep. 22, 1998

[54] PHOTOELECTRIC SYNTHESIS OF DNA OR PROTEIN PROBE ARRAYS

[75] Inventors: Michael Krihak, Phoenix; Chan-Long Shieh, Paradise Valley, both of Ariz.; Hsing-Chung Lee, Calabasas, Calif.

[73] Assignee: Motorola, Inc., Schaumburg, Ill.

[21] Appl. No.: 923,814

[22] Filed: Sep. 4, 1997

[51] Int. Cl.[6] .............................. C25D 5/00; C25D 5/02; C25B 3/00

[52] U.S. Cl. .............................. 205/91; 205/92; 205/118; 205/122; 205/317; 205/340; 205/414; 205/419; 205/424

[58] Field of Search ................. 205/91, 92, 118, 205/122, 317, 414, 419, 424, 340

[56] References Cited

FOREIGN PATENT DOCUMENTS 7-140692  6/1995  Japan .

OTHER PUBLICATIONS

Roget et al., "Electrochemically Directed Copolmerization of Pyrrole and Oligonucleotides", Nucleosides & Nucleotides, 14(3–5), pp. 943–946, 1995.

*Primary Examiner*—Kathryn L. Gorgos
*Assistant Examiner*—Edna Wong
*Attorney, Agent, or Firm*—Eugene A. Parsons

[57] ABSTRACT

A method of photoelectro-synthesizing probe arrays including the steps of providing a photoconductive layer of material having a layer of electrically conductive material on a first surface thereof and a solution of a plurality of a first oligonucleotide modified monomer positioned in electrical contact with an opposing second surface thereof such that a potential is connected therebetween. A beam of light is directed through a portion of the photoconductive layer of material to complete an electrical circuit between the layer of electrically conductive material and the solution through the portion of the photoconductive layer, whereby the monomers in the solution are electropolymerized on a surface area which is coupled into the electrical circuit by the beam of light.

20 Claims, 2 Drawing Sheets

PHOTOELECTRIC SYNTHESIS OF DNA OR PROTEIN PROBE ARRAYS

BACKGROUND OF THE INVENTION

1. Field of the Invention

This invention relates to the fabrication of synthetic DNA or portion probe arrays.

More particularly, the present invention relates to electrochemical deposition of oligonucleotide sequences to form addressed DNA or protein matrices.

2. Prior Art

Currently, the use of oligonucleotides linked to solid supports is widely used particularly to determine DNA sequences for medical diagnostics. The main strategies for fabricating a matrix having numerous oligonucleotides include micro-robotic spotting of modified oligonucleotides micro-droplets on an activated support, in situ synthesis of oligonucleotides using a synthesis mask, and use of a local support photodeprotection and the coupling of a presynthesized oligonucleotide. Each require numerous processing steps and are expensive to perform.

A simpler and more effective process of synthesizing a solid support bearing oligonucleotides has been developed which includes electrochemically directed copolymerization of pyrrole and oligonucleotides bearing a pyrrole group. In this process, a solid support bearing a plurality of independently addressable electrodes is subjected to a solution of oligonucleotides bearing a pyrrole group. The oxidation of the monomer in solution gives in one step, an adherent conducting polymer film deposited on the surface of the working electrodes. Furthermore, the synthesis of this polymer is limited to the electrode surface and can be addressed by the selective switching of the electrodes. This is an extremely effective process, but is limited by the number of addressable electrodes. While large numbers of electrodes and micro-electrodes can be easily formed, addressably contacting each with the use of leads etc. becomes increasingly complex and expensive as the number of electrodes increases.

It would be highly advantageous, therefore, to remedy the foregoing and other deficiencies inherent in the prior art.

Accordingly, it is an object of the present invention to provide a new and improved method of fabricating an addressable DNA probe array.

Another object of the present invention is to provide a method of forming an addressable DNA probe array using wireless contacts for a spatially addressable array of electrodes.

And another object of the present invention is to provide a method of fabricating an addressable DNA probe array which is fast and efficient.

Still another object of the present invention is to provide a method of fabricating large DNA probe arrays.

SUMMARY OF THE INVENTION

Briefly, to achieve the desired objects of the instant invention, in accordance with a preferred embodiment thereof, provided is a method of photoelectro-synthesizing probe arrays including the steps of providing a photoconductive layer of material having a layer of electrically conductive material on a first surface thereof. A solution of a plurality of a first oligonucleotide modified monomer is positioned in electrical contact with a second surface of the photoconductive layer opposed to the first surface and a potential is connected between the solution and the layer of electrically conductive material. A beam of light is directed through a portion of the photoconductive layer of material to complete an electrical circuit between the layer of electrically conductive material and the solution through the portion of the photoconductive layer, whereby the monomers in the solution are electropolymerized on a surface area which is coupled into the electrical circuit by the beam of light.

In another embodiment, the method further includes removing the solution, rinsing the second surface of the photoconductive layer, and providing a second solution having a plurality of a second oligonucleotide modified monomer, different than the plurality of the first oligonucleotide modified monomer, in electrical contact with the second surface of the photoconductive layer. A potential is connected between the second solution and the layer of electrically conductive material, and a beam of light is directed through a second portion of the photoconductive layer of material to complete an electrical circuit between the layer of electrically conductive material and the second solution through the second portion of the photoconductive layer, whereby the monomers in the second solution are electropolymerized on a second surface area which is coupled into the electrical circuit by the beam of light.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
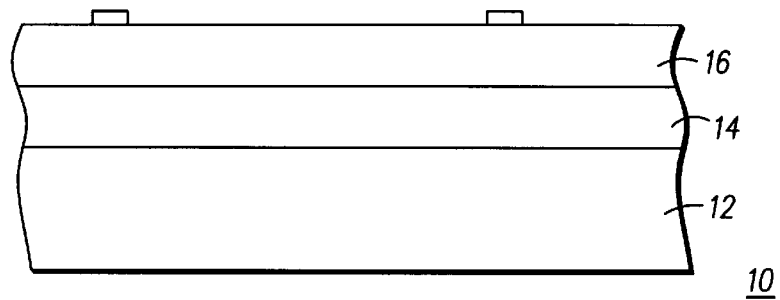
FIG. 1 is a sectional view of a support structure according to the present invention.

Turning now to the drawings in which like reference characters indicate corresponding elements throughout the several views, attention is first directed to FIG. 1 which illustrates a support structure generally designated 10. Support structure 10 includes a substrate 12 preferably fabricated of glass, plastic, etc., a thin conductive layer 14 formed on substrate 12, and a photoconductive layer 16 formed on thin conductive layer 14. Thin conductive layer 14 can be any conductive material such as gold, platinum etc., and can be indium tin oxide (ITO), conductive polymers, or other transparent conductors for reasons which will become apparent from the subsequent description. Photoconductive layer 16 is a material such as amorphous silicon, amorphous SiGe, amorphous SiC, CdS, CdSe, photoconductive polymers, etc. which becomes conductive when subjected to light.

Figure 2:
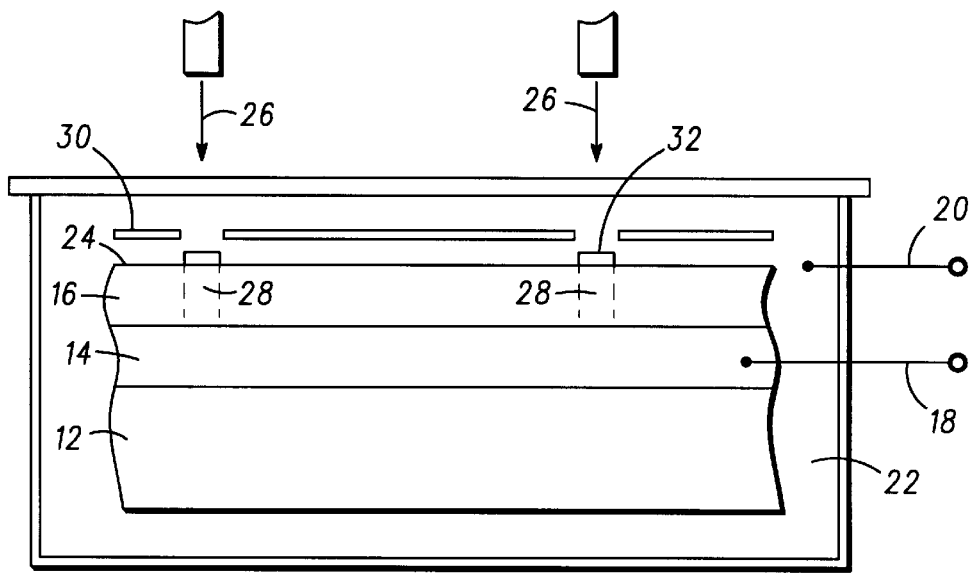
FIG. 2 is a sectional view illustrating the bonding of oligonucleotide modified monomers to the support structure of FIG. 1.

Turning now to FIG. 2, a lead 18 is coupled to conductive layer 14 and a lead 20 is coupled to a solution 22 positioned in electrical contact with a surface 24 of photoconductive layer 16 opposite to conductive layer 14. While not specifically shown in FIG. 2, it will be understood that solution 22 is in electrical contact only with surface 24 and not with conductive layer 14. Furthermore, while support structure 10 is illustrated as being submerged in solution 22, it will be understood that solution 22 can be applied only to surface 24. A potential is applied across leads 20 and 18 and thus between solution 22 and conductive layer 14.

Solution 22 preferably contains a plurality of substantially identical oligonucleotide modified pyrrole monomers, indole, pyrrole derivatives, thiophene, acetylene, aniline, benzene derivatives, or the like. However, it will be understood that most monomers can be modified with an oligonucleotide sequence and used in this process.

Still referring to FIG. 2, a beam or beams of light 26 are directed through a portion 28 of photoconductive layer 16 to complete an electrical circuit between conductive layer 14 and solution 22 through portion 28 of photoconductive layer 16. By completing the circuit, the monomers (pyrrole) in the solution are electropolymerized on, or attracted to and bind with, surface 24 to form a probe 32 within portion 28 which is coupled into the electrical circuit by beam of light 26.

Thus, the present method involves the electropolymerization of oligonucleotide modified pyrrole in an array pattern on support structure 10. The pattern can be determined by the physical placement of a mask 30 adjacent surface 24 of photoconductive layer 16 to block light from selected areas and illuminate portions 28. By placing mask 30 over photoconductive layer 16, a visible laser source can illuminate a region on the order of 10 microns×10 microns. Thus, a plurality of different probes can be formed on different portions of support structure 10. It will be understood that any method of controllably illuminating a selected portion of photoconductive layer 16 can be used, such as the use of a stepper or similar device instead of or in combination with a mask.

Figure 3:
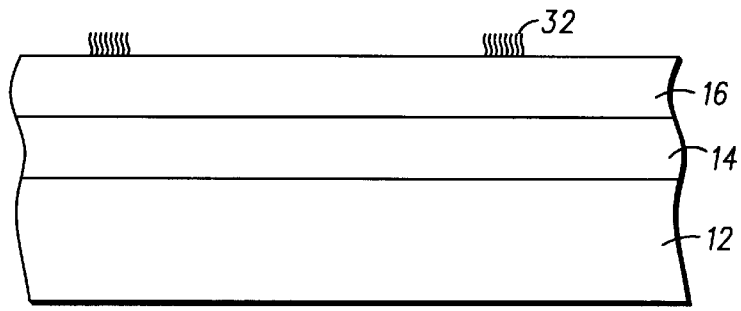
FIG. 3 is a sectional view of the support structure of FIGS. 1 and 2 with probes formed thereon.

Additional probes are added to form an entire array by removing solution 22 and rinsing surface 24 of photoconductive layer 16 to leave probe 32 as illustrated in FIG. 3. Another solution having a plurality of a different oligonucleotide modified monomer is used in a manner as described above, with the light source illuminating a different portion or portions of photoconductive layer 16. This series of steps can be repeated until an array of the desired dimensions is generated.

Figure 4:
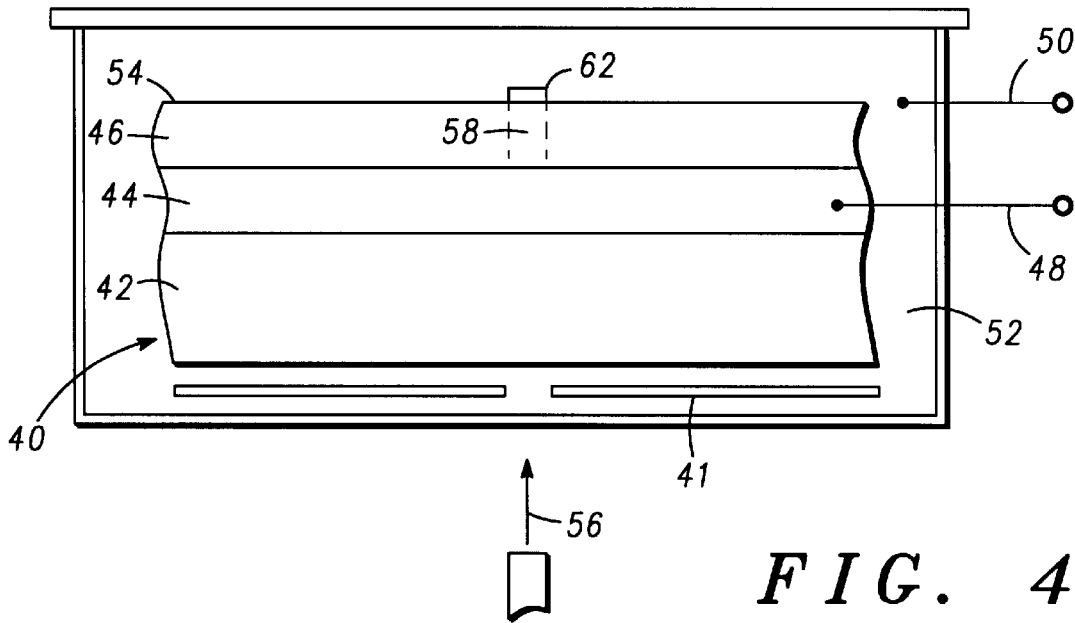
FIG. 4 is a sectional view illustrating another embodiment of the bonding of oligonucleotide modified monomers to a support structure.

In the previously described embodiment, light is directed at photoconductive layer 16 through solution 22. With reference to FIG. 4, another embodiment of a method of the present invention includes directing light through a support structure 40. As with the previous embodiment, the light can be applied as desired by a mask 41 or devices such as a stepper. Support structure 40 includes a substrate 42 formed of a transparent material such as glass, plastic, etc., a thin conductive layer 44 formed on substrate 42, and a photoconductive layer 46 formed on thin conductive layer 44. In this embodiment, thin conductive layer 44 must be a transparent conductor such as indium tin oxide (ITO).

A lead 48 is coupled to conductive layer 44 and a lead 50 is coupled to an oligonucleotide modified monomer solution 52 positioned in electrical contact with a surface 54 of photoconductive layer 46 opposite to conductive layer 44. A potential is applied across leads 48 and 50 and thus between solution 52 and conductive layer 44.

A beam or beams of light 56 are directed through transparent substrate 42, conductive layer 44 and through a portion 58 of photoconductive layer 46 to complete an electrical circuit between conductive layer 44 and solution 52 through portion 58 of photoconductive layer 46. By completing the circuit, the oliginucleotide modified, monomers (pyrrole) in solution 52 are electropolymerized on surface 54 to form a probe 62 within portion 58 which is coupled into the electrical circuit by beam of light 56.

When a beam of light is directed onto portion 58, depending on the source of the light, there can be some diffusion around the edges. This may result in a non-uniform transformation of photoconductive layer 46 between non-conductive and conductive states. This, in turn, can result in non-uniform binding of the monomers.

Figure 5:
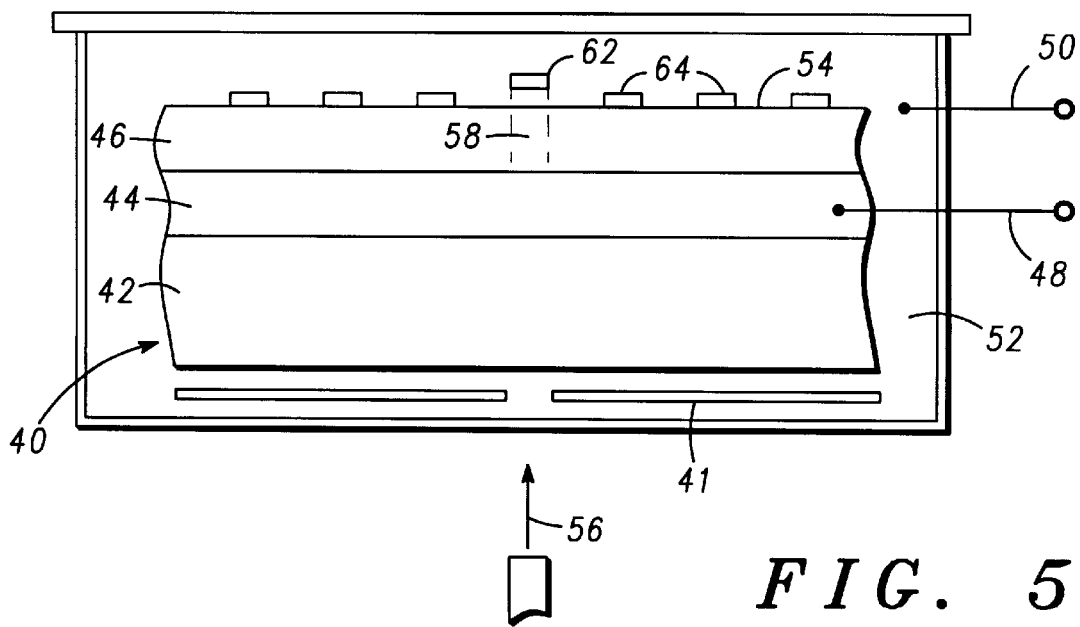
FIG. 5 is a sectional view illustrating yet another embodiment of the bonding of oligonucleotide modified monomers to a support structure.

Turning now to FIG. 5, the embodiment described in connection with FIG. 4 can be modified by patterning surface 54 of photoconductor 46 with a plurality of electrically conductive pads 64 formed in the desired pattern or matrix. The material of electrically conductive pad 64 need not be transparent but can be formed of substantially any conductive material. When an electrical circuit between conductive layer 44 and solution 52 through portion 58 of photoconductive layer 46 is completed, electrically conductive pad 64 in electrical contact with portion 58, uniformly conducts the potential. In this manner, the monomers are uniformly bound to desired ones of electrically conductive pads 64.

It will be understood that each of the previously described methods can be carried out to form a plurality of arrays. Once the plurality of arrays have been formed they can be separated into individual arrays.

The foregoing is given by way of example only. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice the same, the invention claimed is:

1. A method of photoelectro-synthesizing probe arrays comprising the steps of:

providing a photoconductive layer of material having a layer of electrically conductive material on a first surface thereof;

providing a plurality of a first oligonucleotide modified monomer in solution;

positioning the solution in electrical contact with a second surface of the photoconductive layer opposed to the first surface;

connecting a potential between the solution and the layer of electrically conductive material; and directing a beam of light through a portion of the photoconductive layer of material to complete an electrical circuit between the layer of electrically conductive material and the solution through the portion of the photoconductive layer, whereby the monomers in the solution are electropolymerized on a surface area which is coupled into the electrical circuit by the beam of light.

2. A method as claimed in claim 1 further including the steps of:

removing the solution;

rinsing the second surface of the photoconductive layer;

providing a second solution having a plurality of a second oligonucleotide modified monomer, different than the plurality of the first oligonucleotide modified monomer, in electrical contact with the second surface of the photoconductive layer;

connecting a potential between the second solution and the layer of electrically conductive material; and directing a beam of light through a second portion of the photoconductive layer of material to complete an electrical circuit between the layer of electrically conductive material and the second solution through the second portion of the photoconductive layer, where the monomers in the second solution are electropolymerized on a second surface area which is coupled into the electrical circuit by the beam of light.

3. A method as claimed in claim 1 wherein the step of providing the photoconductive layer of material includes providing a transparent substrate, depositing a layer of indium tin oxide (ITO) on the transparent substrate and depositing the photoconductive layer on the layer of ITO.

4. A method as claimed in claim 3 wherein the step of directing the beam of light includes directing the beam of light through the transparent substrate and the layer of ITO.

5. A method as claimed in claim 4 wherein the surface area includes an electrically conductive pad positioned on the portion of the photoconductive layer of material.

6. A method as claimed in claim 4 wherein the step of directing the beam of light further includes providing a mask adjacent the transparent substrate.

7. A method as claimed in claim 1 wherein the photoconductive layer includes one of amorphous silicon, amorphous SiGe, amorphous SiC, CdS, CdSe, or photoconductive polymers.

8. A method as claimed in claim 1 wherein the monomer includes a pyrrole, thiophene, acetylene, aniline, indole, or benzene derivatives.

9. A method as claimed in claim 1 wherein the step of directing a beam of light includes providing a mask.

10. A method of photoelectro-synthesizing probe arrays comprising the steps of:

providing a supporting substrate having a plurality of arrays defined thereon;

positioning an electrically conductive layer on the supporting substrate;

positioning a photoconductive layer on the electrically conductive layer;

providing a plurality of a first oligonucleotide modified monomer in solution;

positioning the solution in electrical contact with the photoconductive layer;

connecting a potential between the solution and the electrically conductive layer; and selecting a first plurality of portions of the photoconductive layer, each of the first plurality of portions being positioned in one of the plurality of arrays defined on the substrate, and directing light through the first plurality of portions of the photoconductive layer to complete a plurality of electrical circuits between the electrically conductive layer and the solution through the first plurality of portions of the photoconductive layer, where the monomers in the solution are electropolymerized on a first plurality of surface areas which are coupled into the plurality of electrical circuits by the light.

11. A method as claimed in claim 10 further including the steps of:

removing the solution;

rinsing the photoconductive layer;

providing a second solution having a plurality of a second oligonucleotide modified monomer, different than the plurality of the first oligonucleotide modified monomer, in electrical contact with the photoconductive layer;

connecting a potential between the second solution and the electrically conductive layer; and selecting a second plurality of portions of the photoconductive layer, each of the second plurality of portions being positioned in one of the plurality of arrays defined on the substrate, and directing light through the second plurality of portions of the photoconductive layer to complete a second plurality of electrical circuits between the electrically conductive layer and the second solution through the second plurality of portions of the photoconductive layer, where the monomers in the second solution are electropolymerized on a second plurality of surface areas which are coupled into the second plurality of electrical circuits by the light.

12. A method as claimed in claim 11 further including the step of separating the plurality of arrays into individual arrays.

13. A method as claimed in claim 10 wherein the step of providing the supporting substrate includes providing a transparent substrate, depositing a layer of indium tin oxide (ITO) on the transparent substrate and depositing the photoconductive layer on the layer of ITO.

14. A method as claimed in claim 13 wherein the step of directing the light includes directing the light through the transparent substrate and the layer of ITO.

15. A method as claimed in claim 14 wherein the first plurality of surface areas include a plurality of electrically conductive pads each positioned on a separate one of the first plurality of portions of the photoconductive layer.

16. A method as claimed in claim 14 wherein the step of directing the light further includes providing a mask adjacent the transparent substrate.

17. A method as claimed in claim 10 wherein the photoconductive layer includes amorphous silicon, amorphous SiGe, amorphous SiC, CdS, CdSe, or photoconductive polymers.

18. A method as claimed in claim 10 wherein the monomer includes a pyrrole, thiophene, acetylene, aniline, indole, or benzene derivatives.

19. A method as claimed in claim 10 wherein the step of directing a beam of light includes providing a mask.

20. A method of photoelectro-synthesizing probe arrays comprising the steps of:

providing a transparent supporting substrate having a plurality of arrays defined thereon;

positioning an electrically conductive layer of indium tin oxide on the supporting substrate;

positioning a photoconductive layer on the electrically conductive layer;

providing a plurality of a first oligonucleotide modified monomer in a first solution;

positioning the first solution in electrical contact with the photoconductive layer;

connecting a potential between the first solution and the electrically conductive layer;

selecting a first plurality of portions of the photoconductive layer, each of the first plurality of portions being positioned in one of the plurality of arrays defined on the substrate, and directing light through the first plurality of portions of the photoconductive layer to complete a plurality of electrical circuits between the electrically conductive layer and the first solution through the first plurality of portions of the photoconductive layer, where the monomers in the first solution are electropolymerized on a first plurality of surface areas which are coupled into the plurality of electrical circuits by the light;

removing the first solution;

rinsing the photoconductive layer;

providing a second solution having a plurality of a second oligonucleotide modified monomer, different than the plurality of the first oligonucleotide modified monomer, in electrical contact with the photoconductive layer;

connecting a potential between the second solution and the electrically conductive layer;

selecting a second plurality of portions of the photoconductive layer, each of the second plurality of portions being positioned in one of the plurality of arrays defined on the substrate, and directing light through the second plurality of portions of the photoconductive layer to complete a second plurality of electrical circuits between the electrically conductive layer and the second solution through the second plurality of portions of the photoconductive layer, where the monomers in the second solution are electropolymerized on a second plurality of surface areas which are coupled into the second plurality of electrical circuits by the light; and separating the plurality of arrays into individual arrays.

* * * * *